United States Patent
Dalloro et al.

(10) Patent No.: US 7,157,397 B2
(45) Date of Patent: Jan. 2, 2007

(54) PROCESS FOR THE PRODUCTION OF MESITYLENE

(75) Inventors: Leonardo Dalloro, Bollate (IT); Alberto Cesana, Carate Brianza (IT); Roberto Buzzoni, San Mauro Torinese (IT); Franco Rivetti, Milan (IT); Giovanni Antonio Fois, Porto Torres (IT); Caterina Rizzo, San Donato Milanese (IT); Virginio Arrigoni, Milan (IT)

(73) Assignees: Polimeri Europa S.p.A., Brindisi (IT); Enitecnologie S.p.A., San Donato Milanese (IT)

( * ) Notice: Subject to any disclaimer, the term of this patent is extended or adjusted under 35 U.S.C. 154(b) by 68 days.

(21) Appl. No.: 10/786,553

(22) Filed: Feb. 26, 2004

(65) Prior Publication Data

US 2004/0225170 A1    Nov. 11, 2004

(30) Foreign Application Priority Data

Feb. 27, 2003  (IT)  .......................... MI2003A0346

(51) Int. Cl.
*B01J 20/34*  (2006.01)

(52) U.S. Cl. ........................................ 502/38; 585/481

(58) Field of Classification Search .................. 502/38; 585/481

See application file for complete search history.

(56) References Cited

U.S. PATENT DOCUMENTS

| 4,152,363 | A |   | 5/1979  | Tabak et al. |
| 5,004,854 | A | * | 4/1991  | Yan ............................. 585/489 |
| 5,206,194 | A |   | 4/1993  | Clark |
| 5,258,566 | A | * | 11/1993 | Kresge et al. .............. 585/467 |

* cited by examiner

*Primary Examiner*—Edward M. Johnson
(74) *Attorney, Agent, or Firm*—Oblon, Spivak, McClelland, Maier & Neustadt, P.C.

(57) ABSTRACT

A process is described for the synthesis of mesitylene, characterized in that mesitylene is obtained starting exclusively from pseudocumene, without the use of any other chemical compound, operating in continuous, at a temperature ranging from 225 to 400° C., at a pressure ranging from 1 to 50 bar, at a weight space velocity ranging from 0.1 to 10 hours$^{-1}$, and in the presence of a catalyst containing a zeolite selected from ZSM-5 zeolite having a crystal lattice based on silicon oxide and aluminum oxide, and ZSM-5 zeolite modified by the partial or total substitution of Si with a tetravalent element such as Ti or Ge and/or the partial or total substitution of Al with other trivalent elements, such as Fe, Ga or B.

17 Claims, 1 Drawing Sheet

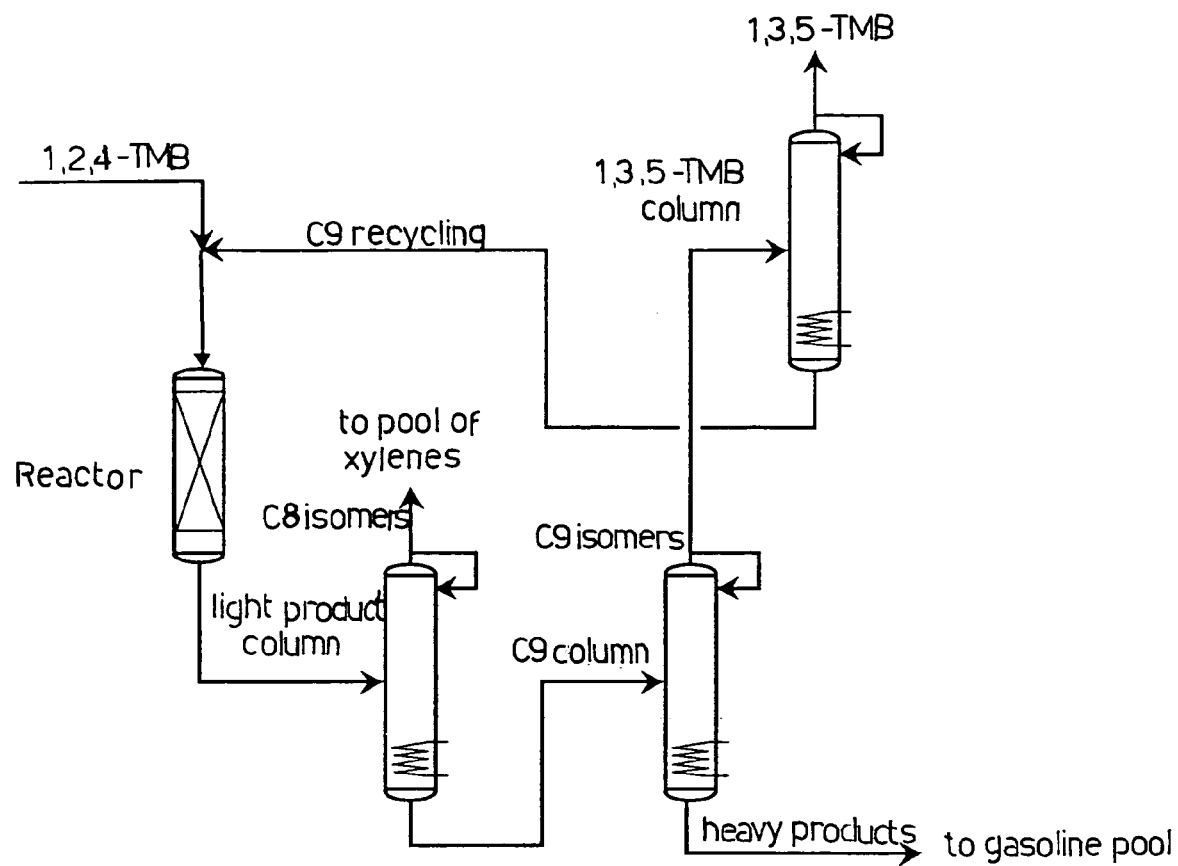
Figure 1 – Plant scheme

PROCESS FOR THE PRODUCTION OF MESITYLENE

The present invention relates to a process for the preparation of mesitylene (1,3,5-trimethyl benzene) starting from pseudocumene (1,2,4-trimethyl benzene), without the use of any other chemical product.

More specifically, the present invention relates to a continuous process, wherein the chemical transformation is carried out in the presence of a catalyst containing a zeolite selected from ZSM-5 zeolite having a crystal lattice made up of silicon oxide and aluminum oxide, and ZSM-5 zeolite modified by the partial or total substitution of Si with a tetravalent element such as Ti or Ge and/or the partial, or total substitution of Al with other trivalent elements such as Fe, Ga or B, in acid form.

Mesitylene is a chemical intermediate, mainly used for the preparation of trimesic acid (or 1,3,5-benzenetricarboxylic acid). This compound, possibly in the form of anhydride, is, in turn, used in the production of plasticizers for polymers and polyimidic, epoxy and polyester resins.

Pseudocumene is obtained by distillation from reforming hydrocarbon streams, in which it is contained in a high concentration.

The same method cannot be applied for the recovery of mesitylene, as the process is not sufficiently advantageous, and it is therefore necessary to resort to an alternative technology.

In particular, the recovery of mesitylene is made critical by the presence of other components of the reforming mixture having very similar volatilities, mainly the three ethyl-methylbenzene isomers and above all 2-ethylmethylbenzene.

The alternative technologies are based on chemical reactions.

Mesitylene can be obtained by dehydration and condensation of acetone on catalysts based on tantalum (GB 852,674) or based on niobium (U.S. Pat. No. 5,087,781, GB 931,893); the process produces high concentrations of mesitylene, but uses three reagent molecules for each molecule of mesitylene produced and can only be advantageous for producers having acetone at a low cost.

The patents U.S. Pat. No. 2,873,300, U.S. Pat. No. 3,189,659 and U.S. Pat. No. 3,987,120 describe the recovery of mesitylene from reforming hydrocarbon streams based on sulfonation processes with concentrated sulfuric acid. These processes have scarce industrial use due to the formation of considerable quantities of acid by-products.

U.S. Pat. No. 2,589,621 describes the preparation of mesitylene from an isomer of trimethyl benzene, such as pseudocumene, through isomerization in liquid phase in the presence of HF and $BF_3$. This process has the drawback of using an extremely corrosive and dangerous catalytic system U.S. Pat. No. 3,253,049 describes the production of mesitylene from pseudocumene by means of isomerization carried out on a catalyst based on platinum, supported on alumina containing chlorine, in the presence of hydrogen in order to reduce coke formation phenomena. The process has the drawback of using hydrogen and a catalyst containing a noble metal such as platinum.

U.S. Pat. No. 3,637,880 describes a process for the preparation of mesitylene starting from hydrocarbon mixtures of xylenes and pseudocumene, carried out in the presence of crystalline aluminum silicates. According to the disclosure of this patent, the addition of xylenes is useful for hindering the transalkylation reaction, but has, in turn, evident disadvantages relating to the separation and dimensioning of the equipment, as the amount of xylenes added can reach 35%.

U.S. Pat. No. 5,004,854 describes a process for recovering pseudocumene and mesitylene from a $C_9$ aromatic cut, containing propyl benzenes and ethyl methyl benzenes, by means of treatment with hydrogen in the presence of a zeolite having an Si/Al ratio of at least 12 and a constraint index of 1 to 12, so as to convert the propyl benzenes and ethyl methyl benzenes, thus forming a product mix containing benzene, toluene, $C_8$-$C_9$-$C_{10}$ alkyl benzenes, from which mesitylene and pseudocumene are recovered. The catalyst is preferably a ZSM-5 zeolite containing a metal with hydrogenating function such as platinum, nickel, molybdenum, cobalt or zinc. This process also has the drawback of using hydrogen and a catalyst containing a metal with a hydrogenating function.

The process object of the present invention comprises the chemical transformation of pseudocumene to mesitylene, using a catalyst containing a zeolite selected from ZSM-5 zeolite with a crystal lattice made up of silicon oxide and aluminum oxide, and ZSM-5 zeolite modified by the partial or total substitution of Si with a tetravalent element such as Ti or Ge and/or the partial or total substitution of Al with other trivalent elements such as Fe, Ga or B. The production of mesitylene is therefore carried out starting from pseudocumene, without using any other chemical product and, unexpectedly, takes place without any significant production of coke, making it possible to operate with a constant catalytic activity for very long working cycles.

It is generally well known, moreover, that isomerization reactions can be followed by disproportioning reactions, in particular transalkylation, which negatively influence the selectivity results which can be obtained. By using the catalytic compositions of the present invention, high selectivities are unexpectedly obtained to the desired product mesitylene, whereas the products deriving from transalkylation processes, such as durene and xylenes, are formed in reasonably low quantities.

An object of the present invention therefore relates to a process for the synthesis of mesitylene, which comprises the treatment of pseudocumene with a catalytic composition containing a zeolite selected from ZSM-5 zeolite with a crystal lattice based on silicon oxide and aluminum oxide, and ZSM-5 zeolite modified by the partial or total substitution of Si with a tetravalent element such as Ti or Ge and/or the partial or total substitution of Al with other trivalent elements such as Fe, Ga or B, said zeolite being in acid or prevalently acid form.

The ZSM-5 zeolite with a crystal lattice based on silicon oxide and aluminum oxide is described in U.S. Pat. No. 3,702,886 and in the re-issue Re Pat. No. 29,948.

Reference to the structure of ZSM-5 zeolite can also be found in "Atlas of Zeolite Framework Types" Ch. Baerlocher, W. M. Meier and D. H. Olson, Fifth Revised Edition 2001, Elsevier Amsterdam.

ZSM-5 zeolites with a crystal lattice based on silicon oxide and gallium oxide, ZSM-5 zeolites with a crystal lattice based on germanium oxide and aluminum oxide and ZSM-5 zeolites with a crystal lattice based on germanium oxide and gallium oxide, are also described in U.S. Pat. No. 3,702,886.

ZSM-5 zeolites with a crystal lattice made up of silicon oxide, titanium oxide and aluminum oxide are described in EP 226,257.

EP 226,258 describes ZSM-5 zeolites with a crystal lattice based on silicon oxide, titanium oxide and iron oxide.

ZSM-5 zeolites with a crystal lattice made up of silicon oxide, titanium oxide and gallium oxide are described in EP 266,825.

U.S. Pat. No. 4,656,016 describes ZSM-5 zeolites with a crystal lattice based on silicon oxide and iron oxide. The same patent also describes ZSM-5 zeolites with a crystal lattice made up of silicon oxide and boron oxide.

Syntheses of ZSM-5 zeolite modified by the partial or total substitution of Si with a tetravalent element such as Ti or Ge and/or the partial or total substitution of Al with other trivalent elements such as Fe, Ga or B are also described, for example, in Bellussi et al. in Stud. Surf. 56. Catal. 63 (1991) 421; S. Li et al. in Micropor. Mesopor. Mater. 58 (2003) 137–154; Brückner et al. in Zeolites 12 (1992) 380; D. Trong On et al. in Micropor. Mesopor. Mater. 57 (2003) 169–180; V. R. Choudhary et al. in Micropor. Mesopor. Mater. 57 (2003) 317–322.

Normally, these modifications of ZSM-5 zeolites can be obtained by partially or totally substituting the Si sources with Ti or Ge sources, and/or by partially or totally substituting the aluminum sources with Fe, Ga or B sources in the synthesis processes described in U.S. Pat. No. 3,702,886, EP 226,257, EP 226,258 and EP 266,825.

The use of ZSM-5 zeolite with a crystal lattice based on silicon oxide and aluminum oxide is a preferred aspect of the present invention. The molar ratio between silicon oxide and aluminum oxide is preferably higher than 20. ZSM-5 zeolites having a ratio between silicon oxide and aluminum oxide ranging from 20 to 1,000, preferably from 25 to 300, are suitably used.

The zeolites of the ZSM-5 type used in the catalytic compositions of the present invention are in acid or prevalently acid form, i.e. with all or most of the synthesis cations substituted by hydrogen ions. The substitution can be conveniently effected, for example, by means of ion exchange with ammonium ions and subsequent calcination, as is well known in the state of the art.

The process object of the invention is carried out at a temperature ranging from 225 to 400° C., preferably from 250 to 375° C. The process is carried out at a pressure ranging from 1 to 50 bar, preferably at a pressure generally ranging from 5 to 50 bar.

A preferred aspect of the present invention is for the process to be carried out in liquid phase.

The feed consists of pure pseudocumene or, as can be seen hereafter, in a mixture with other recycled compounds deriving from the process itself. The feeding flow-rate is suitably selected, together with the other process variables, in relation to the desired conversion grade. For the feed, a space velocity (WHSV=Weight Hourly Space Velocity, expressed as kg of hydrocarbon mixture/hour/kg of catalyst) of between 0.1 and 10 hours$^{-1}$ can be used.

The process is preferably carried out in continuous, in a fixed bed reactor and, as the enthalpy of the process is not particularly high, particular expedients for the thermal exchange are not required; what is normally known as an industrial adiabatic reactor is therefore adequate.

In this case, the zeolitic material contained in the catalyst is conveniently formed by mixing, according to the known techniques, the zeolite in the form of crystal powder, with an inorganic binder which is sufficiently inert with respect to the reagents and products, for example silica, alumina, zirconia, magnesia and mixtures thereof.

Alumina is the preferred binder, and it can be introduced into the catalytic composition through one of its precursors, such as bohemite or pseudo-bohemite, for example, which produces alumina by calcination.

In the preparation of the catalytic composition, the zeolite is preferably used in ammonia form, which is converted to the corresponding acid form by calcination.

The ratio between the active phase, consisting of the zeolite, and the binder, can be maintained within a ratio of 5:95 to 95:5 by weight, preferably from 20:80 to 80:20, by weight.

A form and dimension suitable for use in an industrial reactor is given to the zeolite/binder composite material, mainly for the purpose of obtaining a low pressure drop and a suitable mechanical resistance and resistance to abrasion. For the purposes of the present invention, any process for the production of spherulites, extrusion, tableting and granulation process known in the state of the art is suitable for the purpose, but extrusion is the preferred process. Extrusion processes comprise the use of a peptizing agent which is paste-mixed with the zeolite, preferably in ammonia form, and the binder, until a homogeneous paste is obtained, ready to be extruded.

For the purposes of the present invention, it is not necessary to obtain extruded products of a certain length or section, cylinders of 2–6 mm in diameter and 2–20 mm in length are suitable for the purposes of the invention.

The extrusion is followed by a calcination step, according to the known techniques.

With the catalysts and operating conditions described above, the catalytic activity can be maintained for long periods of time (several thousands of hours), without requiring any particular interventions or operative procedures for restoring the catalytic activity. In particular, the methods disclosed by the state of the art for maintaining the catalytic activity for long periods of time, such as impregnation of the catalyst with metals typically used for hydrogenation reactions (such as Ni, Pt, etc.) and the addition of hydrogen to the reaction mixture, as described, for example, in U.S. Pat. No. 4,891,467, are not necessary.

The catalytic life can be prolonged by gradually increasing the temperature at which the process is carried out, for example by 2–4° C. every 100 hours of operation. Subsequently, when the catalyst begins showing at least partial deactivation, the duration of the catalytic activity can be further prolonged by carrying out operating periods at a temperature at least 40° C. higher than that at which the catalyst starts showing deactivation, and for a time period of between 100 and 300 hours. During this time, a substantial rejuvenation of the catalyst takes place, at the end of which the preceding temperature conditions can be restored. This rejuvenation treatment proves to be particularly useful when the pre-selected operating conditions comprise operating at a low WHSV and contemporaneously at a low temperature, and it can be cyclically repeated to maximize the benefit.

It has also been surprisingly found that the catalyst reaction cycle can be further prolonged if the pseudocumene is suitably de-oxygenated before being fed. A process useful for this purpose is that described in EP 0780354 for the alkylation of aromatic compounds with olefins, i.e. degassing by saturation with inert gas (such as nitrogen), but also degassing by boiling or direct use after distillation, without intermediate storage. These processes allow the deactivation to be minimized, even at low temperatures.

The catalyst can in any case be subjected to regeneration treatment: the most suitable method is the combustion of the carbonaceous deposits which have accumulated during use, according to what is known in the state of the art, by operating, for example, at a temperature ranging from 450 to 550° C., at a pressure ranging from 1 to 3 bar, with oxygen and nitrogen mixtures in a ratio ranging from 0.1 to 20% by weight and a space velocity (GHSV=Gas Hourly Space Velocity, expressed in l of gas mixture/hour/l of catalyst) of between 3000 and 6000 hours$^{-1}$. Considering the low regeneration frequency, it not necessary to effect the regeneration in the same reactor in which the catalyst is introduced for the reaction, the catalyst can be discharged during periodical maintenance phases of the plant and regenerated elsewhere, and in this way the reactor can be constructed without control devices necessary for effecting the regeneration.

The reaction which takes place in the process, object of the invention, is an isomerization reaction.

The isomerization of pseudocumene leads to the formation of mesitylene and hemimellitene (1,2,3-trimethylbenzene); a mixture of the three isomers of trimethylbenzene is therefore generated, hereinafter called, for the sake of brevity, "$C_9$ isomers".

Even if the production is carried out starting from pseudocumene, as described below, hemimellitene produced by the process itself and recycled after separation from mesitylene, can also be possibly fed together with pseudocumene. Hemimellitene, in fact, analogously to pseudocumene, undergoes isomerization to generate mesitylene.

According to a preferred embodiment of the invention, a fraction of light products, $C_8$ isomers, an intermediate fraction also containing non-converted pseudocumene, $C_9$ isomers and a heavier fraction containing hydrocarbons with a molecular weight higher than that of the $C_9$ isomers, are separated from the reaction raw material by means of distillation. Mesitylene is recovered from the $C_9$ isomers by distillation at a purity suitable for industrial use (>99%), whereas the remaining part of $C_9$ isomers (mainly hemimellitene and pseudocumene) is recycled to the process itself.

As far as the fraction of $C_8$ isomers is concerned, this is not recycled to the process itself, but, according to the logic of a petrochemical plant which exploits reforming streams, is destined to be integrated into the stream of xylenes. In the same way, the residue of heavy hydrocarbons of the distillation of the raw material is sent to the fuel stream.

FIG. 1 shows a possible scheme of the process, object of the invention, according to what has been stated above.

In this figure, 1,2,4-TMB is the pseudocumene which feeds the reactor (reactor). The light column is the distillation column which separates the $C_8$ isomers to recover them from the reaction raw material and send them to the pool of xylenes. The $C_9$ column is the distillation column which separates the $C_9$ fraction from the remaining of the reaction raw product, which is recovered as fuel (fraction sent to the gasoline pool). The 1,3,5-TMB column is the distillation column which separates mesitylene (1,3,5-TMB) from the remaining $C_9$ isomers, which are recycled to the reactor.

A further characterizing element of the process is to operate exclusively with mixtures of benzene methyl derivatives. Unlike what happens when mixtures having a complex composition are rearranged, the possibility of operating exclusively with trimethylbenzenes (1,2,4trimethylbenzene, 1,2,3 trimethylbenzene) provides benefits in all the process phases, in particular those relating to the purification of the products, as the number of benzene derivatives is much lower and the fractionation of the reaction raw material much simpler. In particular, in the absence of benzene derivatives, such as ethyl-methylbenzenes, the separation and purification of mesitylene by distillation of the $C_9$ cut is extremely simplified.

Finally, it should also be remembered that the method used makes it possible to operate at the highest concentration of the compounds of interest and to reduce as much as possible the dimensions of the reactor and other equipment, which is an important advantage considering that all the reactions in question are already jeopardized by being equilibrium reactions.

The same advantages in the separation of the final product and in the dimensions of the equipment are further enhanced by the possibility of operating without the addition of xylenes in the feed of trimethylbenzenes, as described in the prior art.

Some illustrative examples are provided hereunder for a better understanding of the present invention, but should in no way be considered as limiting the scope of the invention itself.

EXAMPLE 1

Synthesis of H-ZSM-5 Zeolite in Industrial Size

A catalyst based on ZSM-5 zeolite in acid form (H-ZSM-5) and in an industrial size was prepared according to the following procedure.

315.4 g of a commercial zeolite ($NH_4$-ZSM-5, $SiO_2$/$Al_2O_3$=/30, CBV 3024E Zeolyst, the characteristics are shown in Table 1 below) and 438 g of an alumina precursor in the form of bohemite (La Roche VERSAL 150) were mixed, under dry conditions, for 60 minutes. 380 ml of a solution of acetic acid 1% (v/v) were added as peptizing agent and the mixture was mixed for a further 36 minutes.

TABLE 1

| | |
|---|---|
| Zeolite: | ZSM-5 |
| Producer: | ZEOLYST |
| Name: | $NH_4$-ZSM-5 ZEOLYST ™ CBV3024E |
| $SiO_2$/$Al_2O_3$ ratio: | 30 mole/mole |
| Form: | powder |

The mixture was then extruded and calcined at 550° C. for 4 hours. In this way, a catalyst was obtained of a cylindrical form, with a diameter of about 2 mm, containing about 50% of H-ZSM-5 zeolite. The extruded catalyst thus obtained has a hardness along the diameter of 12.7 Kg/cm, and an extra-zeolitic porosity of 0.4 ml/g.

The catalyst was ground to 14–35 mesh, before its use in a laboratory reactor.

EXAMPLES OF CATALYTIC PERFORMANCES

The catalytic activity tests described in the following examples were carried out in experimental laboratory equipment, in which the operating conditions to be used for the best process running can be studied.

Pseudocumene was fed in the tests, having a titre of >99% by weight; the composition of the feeding mixture used is indicated in Table 2, wherein Σ<C8 are the compounds having a molecular weight lower than that of xylenes, ΣC8 are xylenes, 135-TMB is mesitylene, 124-TMB is pseudocumene, 123-TMB is hemimellitene, ΣC10 are trimethylbenzenes, Σ>C10 are compounds having a molecular weight higher than that of the $C_{10}$ isomers.

TABLE 2

| Feeding mixture composition (weight %) | | | | | | |
|---|---|---|---|---|---|---|
| Σ < C8 | Σ C8 | 135-TMB | 124-TMB | 123-TMB | Σ C10 | Σ > C10 |
| 0.2 | 0.0 | 0.1 | 99.2 | 0.1 | 0.0 | 0.0 |

The equipment and operating conditions are described below.

Catalytic Test: Equipment and Operating Conditions

The isomerization reaction of pseudocumene is carried out in a tubular, fixed bed micro-reactor, having the following characteristics: material=inox steel AISI 316L, length 180 mm, $\varnothing_{int.}$=12 mm, thermocouple sheath with $\varnothing_{ext.}$=3 mm. The reactor is placed in a oven which allows it to be brought to the temperature selected for the reaction.

The catalyst used for the test has a size of <2 mm. The catalyst charge is 2÷8 g and it is placed in the reactor between two layers of granular quartz.

The feeding is pre-heated before being introduced into the lower part of the reactor and before coming into contact with the catalyst; the flow rate is controlled by means of a pump of the HPLC type.

The pressure of the plant is controlled by a regulation valve at the outlet of the reactor.

In the starting phase of the activity test, the catalyst is heated to the reaction temperature under a dry nitrogen flow, at low pressure, for 1 hour. The feeding of pseudocumene is subsequently started.

The hydrocarbon mixture flowing from the pressure regulation valve, is cooled and samples of reaction raw material are collected for the evaluation of the catalytic performances.

The samples are analyzed by gas-chromatography, and the catalytic performances are evaluated by calculating the composition of the mixture, the ratios between the isomers, the conversion and yield to the two compounds of interest.

The regeneration of the catalyst after the activity test, was carried out in the same reactor used for the reaction. The operating conditions are the following: temperature=450÷550° C., pressure=1÷3 bar, oxygen concentration=0.1÷20% and GHSV space velocity=3000÷6000 hours$^{-1}$. In particular, the treatment starts with a stream of nitrogen alone, to which an equal stream of air is progressively added (in about 1 hour), the nitrogen stream is then progressively reduced until it is annulled (in about 1 hour) and the treatment is prolonged for 5 to 24 hours, in relation to the duration of the preceding activity test. At the end of the treatment, the reactor is washed with a nitrogen flow, and the catalytic activity test can be restarted.

EXAMPLES 2–5

Catalytic Activity Test

Some examples of catalytic activity tests are provided below, using a catalyst corresponding to the characteristics of the present invention. The results obtained in a life test are also indicated.

The catalytic performances obtained using a catalyst based on zeolite ZSM-5, at 50% of active phase, whose preparation is described in Example 1, are shown in the following Tables 3–6

The results, obtained at different temperatures and WHSV, demonstrate that this catalyst can be advantageously used for the purposes of the present invention (the operating conditions are indicated in the same tables).

TABLE 3

Examples 2/1–2/4

OPERATING CONDITIONS

| Catalyst | ZSM-5 Zeolite, See Ex. 1 |
|---|---|
| Reaction temperature (° C.) | 275–340 |
| WHSV (hours$^{-1}$) | 1.0 |
| Pressure (bar) | 50 |
| Feeding mixture | See Table 2 |

CATALYTIC PERFORMANCES

| Ex Nr. | React. temp. ° C. | Reaction raw material composition (molar %) | | | | | | |
|---|---|---|---|---|---|---|---|---|
| | | Σ < C8 | Σ C8 | 135-TMB | 124-TMB | 123-TMB | Σ C10 | Σ > C10 |
| 2/1 | 275 | 0.2 | 1.0 | 7.0 | 88.2 | 2.8 | 0.4 | 0.2 |
| 2/2 | 320 | 0.3 | 2.8 | 22.7 | 63.7 | 8.1 | 1.3 | 0.6 |
| 2/3 | 330 | 0.5 | 4.2 | 23.6 | 60.1 | 8.3 | 2.1 | 1.0 |
| 2/4 | 340 | 0.6 | 5.5 | 23.2 | 57.8 | 8.2 | 3.0 | 1.4 |

TABLE 4

Examples 3/1–3/6

OPERATING CONDITIONS

| Catalyst | ZSM-5 Zeolite, See Ex. 1 |
|---|---|
| Reaction temperature (° C.) | 290–340 |
| WHSV (hours$^{-1}$) | 2.0 |
| Pressure (bar) | 50 |
| Feeding mixture | See Table 2 |

TABLE 4-continued

Examples 3/1–3/6

CATALYTIC PERFORMANCES

| Ex Nr. | React. temp. ° C. | Reaction raw material composition (molar %) | | | | | |
|---|---|---|---|---|---|---|---|
| | | Σ < C8 | Σ C8 | 135-TMB | 124-TMB | 123-TMB | Σ C10 | Σ > C10 |
| 3/1 | 290 | 0.1 | 0.9 | 7.5 | 88.0 | 3.0 | 0.1 | 0.0 |
| 3/2 | 300 | 0.2 | 1.1 | 10.9 | 82.9 | 4.3 | 0.2 | 0.1 |
| 3/3 | 310 | 0.2 | 1.4 | 14.7 | 77.0 | 5.7 | 0.4 | 0.1 |
| 3/4 | 320 | 0.3 | 1.8 | 19.0 | 70.3 | 7.2 | 0.7 | 0.3 |
| 3/5 | 330 | 0.4 | 3.5 | 23.0 | 61.9 | 8.3 | 1.7 | 0.8 |
| 3/6 | 340 | 0.5 | 4.2 | 23.4 | 59.8 | 8.4 | 2.2 | 1.0 |

Table 5 indicates the operating conditions and catalytic performances obtained in a test lasting 1200 hours, with the catalyst based on ZSM-5 zeolite, with 50% of active phase, prepared according to Example 1. In this table, TOS (Time On Stream) indicates the working time of the catalyst.

The first cycle of the life test was effected for about 1200 hours with no regeneration of the catalyst.

After the life test, the catalyst was regenerated. The regeneration was carried out according to the method described above, in the paragraph dedicated to the operating

TABLE 5

Examples 4/1–4/14

OPERATING CONDITIONS

| Catalyst | ZSM-5 Zeolite, See Ex. 1 |
|---|---|
| Reaction temperature (° C.) | 330–335 |
| WHSV (hours$^{-1}$) | 2.0 |
| Pressure (bar) | 50 |
| Feeding mixture | See Table 2 |

CATALYTIC PERFORMANCES

| Ex Nr. | TOS (hours) | Reaction raw material composition (molar %) | | | | | |
|---|---|---|---|---|---|---|---|
| | | Σ < C8 | Σ C8 | 135-TMB | 124-TMB | 123-TMB | Σ C10 | Σ > C10 |
| Reaction temperature = 330° C. from Ex. 4/1 to Ex. 4/12 | | | | | | | | |
| 4/1 | 145 | 0.4 | 3.5 | 23.0 | 61.9 | 8.3 | 1.7 | 0.8 |
| 4/2 | 210 | 0.4 | 2.9 | 23.3 | 62.3 | 8.5 | 1.6 | 0.7 |
| 4/3 | 297 | 0.3 | 2.4 | 23.0 | 63.4 | 8.4 | 1.4 | 0.6 |
| 4/4 | 378 | 0.2 | 2.0 | 22.8 | 64.2 | 8.4 | 1.3 | 0.6 |
| 4/5 | 477 | 0.3 | 2.0 | 22.6 | 64.7 | 8.4 | 1.2 | 0.5 |
| 4/6 | 567 | 0.3 | 2.0 | 22.8 | 64.4 | 8.3 | 1.2 | 0.5 |
| 4/7 | 653 | 0.3 | 2.0 | 22.9 | 64.3 | 8.5 | 1.3 | 0.6 |
| 4/8 | 748 | 0.3 | 2.1 | 23.1 | 63.9 | 8.5 | 1.3 | 0.6 |
| 4/9 | 832 | 0.3 | 1.8 | 22.4 | 65.0 | 8.4 | 1.1 | 0.5 |
| 4/10 | 871 | 0.3 | 1.7 | 22.3 | 65.4 | 8.3 | 1.0 | 0.4 |
| 4/11 | 962 | 0.3 | 1.6 | 22.1 | 65.9 | 8.3 | 0.9 | 0.4 |
| 4/12 | 1049 | 0.3 | 1.4 | 21.5 | 67.1 | 8.1 | 0.8 | 0.4 |
| Reaction temperature = 332° C. in Ex. 4/13 | | | | | | | | |
| 4/13 | 1069 | 0.3 | 1.6 | 22.1 | 65.7 | 8.3 | 1.0 | 0.4 |
| Reaction temperature = 335° C. in Ex. 4/14 | | | | | | | | |
| 4/14 | 1083 | 0.3 | 1.9 | 22.9 | 64.2 | 8.5 | 1.2 | 0.5 |

The results of the life test demonstrate the stability of the performances of the catalyst and the selectivity of the isomerization process with respect to the competing transalkylation reaction. The ratio between mesitylene (135-TMB) and the sum of xylenes produced (Σ C8), which passes from 6.6 mole/mole at the beginning of the test, to >10 mole/mole after 300 TOS hours and reaches 15.4 mole/mole at the 1049$^{th}$ hour, can be used as selectivity index.

conditions of the catalytic test, (in particular, the temperature was maintained at 480° C., the pressure at 1 bar, the GHSV at 3000 hours$^{-1}$ and the treatment was prolonged for 12 hours). Table 6 shows the performances reached with the regenerated catalyst, obtained in the second reaction cycle, and they can be compared with those of the first cycle indicated in Table 5 above: the complete recovery of the catalytic performances is evident.

TABLE 6

Examples 5/1–5/2

OPERATING CONDITIONS

| Catalyst | ZSM-5 Zeolite, See Ex. 1 |
|---|---|
| Reaction temperature (° C.) | 330 |
| WHSV (hours$^{-1}$) | 2.0 |
| Pressure (bar) | 50 |
| Feeding mixture | See Table 2 |

CATALYTIC PERFORMANCES

| Ex Nr. | TOS (hours) | Reaction raw material composition (molar %) | | | | | |
|---|---|---|---|---|---|---|---|
| | | Σ < C8 | Σ C8 | 135-TMB | 124-TMB | 123-TMB | Σ C10 | Σ > C10 |
| 5/1 | 1200 + 117 | 0.4 | 3.3 | 23.3 | 61.9 | 8.4 | 1.6 | 0.7 |
| 5/2 | 1200 + 167 | 0.4 | 2.9 | 23.4 | 62.5 | 8.4 | 1.5 | 0.7 |

The invention claimed is:

1. A liquid phase process for the synthesis of mesitylene in the absence of added hydrogen which comprises treating pseudocumene with a catalytic composition comprising a zeolite, in acid or prevalently acid form, selected from ZSM-5 zeolite having a crystal lattice made up of silicon oxide and aluminum oxide, and ZSM-5 modified by the partial or total substitution of Si with a tetravalent element and/or the partial or total substitution of Al with other trivalent elements, wherein said process is carried out exclusively in the liquid phase at a temperature of from 250 to 375° C. and a pressure of between 5 and 50 bar, and wherein said process is conducted in the absence of added hydrogen.

2. The process according to claim 1, wherein the catalytic composition comprises ZSM-5 zeolite having a crystal lattice made up of silicon oxide and aluminum oxide.

3. The process according to claim 2, wherein the molar ratio between silicon oxide and aluminum oxide is higher than 20.

4. The process according to claim 3, wherein the molar ratio between silicon oxide and aluminum oxide ranges from 20 to 1000.

5. The process according to claim 4, wherein the molar ratio between silicon oxide and aluminum oxide ranges from 25 to 300.

6. The process according to claim 1, wherein the catalytic composition comprises the zeolite in a bound form, with a binder selected from alumina, silica, magnesia, zirconia or mixtures thereof.

7. The process according to claim 6, wherein the weight ratio between zeolite and binder ranges from 5:95 to 95:5.

8. The process according to claim 7, wherein the weight ratio ranges from 20:80 to 80:20.

9. The process according to claim 1, wherein the WHSV space velocity is between 0.1 and 10 hours$^{-1}$.

10. The process according to claim 1, carried out continuously, in a fixed bed reactor.

11. The process according to claim 1, wherein the pseudocumene is de-oxygenated before being treated with the catalytic composition.

12. The process according to claim 11, wherein the pseudocumene is de-oxygenated by means of degassing by saturation with an inert gas or by boiling.

13. The process according to claim 1, wherein the pseudocumene used comes directly from distillation, without intermediate storage.

14. The process according to claim 1, wherein said catalytic composition comprises ZSM-5 modified by the partial or total substitution of Si with a tetravalent element and/or the partial or total substitution of Al with other trivalent elements.

15. The process according to claim 14, wherein said catalytic composition comprises ZSM-5 modified by the partial or total substitution of Si with Ti or Ge and/or the partial or total substitution of Al with Fe, Ga or B.

16. The process according to claim 1, wherein said process consists essentially of contacting said catalytic composition with said pseudocumene.

17. A process for regenerating a catalyst, at least partially exhausted, which comprises treating said catalyst at a temperature ranging from 450 to 550° C., at a pressure ranging from 1 to 3 bar, with mixtures of oxygen and nitrogen in a ratio ranging from 0.1 to 20% by volume, and with a GHSV space velocity of between 3000 and 6000 hours$^{-1}$, wherein said catalyst is a catalyst previously used in a process for the synthesis of mesitylene which comprises treating pseudocumene with a catalytic composition comprising a zeolite, in acid or prevalently acid form, selected from ZSM-5 zeolite having a crystal lattice made up of silicon oxide and aluminum oxide, and ZSM-5 modified by the partial or total substitution of Si with a tetravalent element and/or the partial or total substitution of Al with other trivalent elements.

* * * * *